US009783769B2

(12) United States Patent
Clark et al.

(10) Patent No.: US 9,783,769 B2
(45) Date of Patent: Oct. 10, 2017

(54) LAYERED FLASK CELL CULTURE SYSTEM

(75) Inventors: Phillip Clark, Wakefield, MA (US); Kurt Greenizen, Bradford, MA (US); Christopher A. Scott, Westford, MA (US); Marc Emerick, Amesbury, MA (US)

(73) Assignee: EMD Millipore Corporation, Billerica, MA (US)

( * ) Notice: Subject to any disclaimer, the term of this patent is extended or adjusted under 35 U.S.C. 154(b) by 797 days.

(21) Appl. No.: 12/460,265

(22) Filed: Jul. 16, 2009

(65) Prior Publication Data

US 2010/0129900 A1    May 27, 2010
US 2016/0137961 A2    May 19, 2016

Related U.S. Application Data

(60) Provisional application No. 61/207,683, filed on Feb. 14, 2009, provisional application No. 61/134,985, filed on Jul. 16, 2008.

(51) Int. Cl.
*C12M 1/24* (2006.01)
*C12M 1/00* (2006.01)
(Continued)

(52) U.S. Cl.
CPC ............ *C12M 23/08* (2013.01); *C12M 21/08* (2013.01); *C12M 23/04* (2013.01); *C12M 23/22* (2013.01);
(Continued)

(58) Field of Classification Search
CPC ....... C12M 23/04; C12M 25/06; C12M 23/08
(Continued)

(56) References Cited

U.S. PATENT DOCUMENTS 4,228,243 A * 10/1980 Iizuka ................... C12M 23/34
                                                                435/294.1
4,770,854 A *  9/1988 Lyman .................. C12M 23/44
                                                                215/10
(Continued)

FOREIGN PATENT DOCUMENTS

WO     88/00235 A1    1/1988
WO     92/05243 A1    4/1992
(Continued)

OTHER PUBLICATIONS

International search Report and Written Opinion received for PCT Patent Application No. PCT/US2009/004118, mailed on Apr. 9, 2010, 8 pages.
(Continued)

*Primary Examiner* — Jonathan Hurst
(74) *Attorney, Agent, or Firm* — EMD Millipore Corporation

(57) ABSTRACT

The present invention is a cell cultivating vessel or device, such as a single or multitier flask, including a cover having a top plate, a side wall and a resealable port; an intermediate tray for receiving cells and cell culture media, having a bottom plate, a side wall, and a gap region formed between an interior upwardly angled lip located on an interior portion of the intermediate tray bottom plate and an adjacent outwardly angled side wall portion of the intermediate tray bottom plate, wherein the lip has a outwardly swooping curvilinear edge feature; and a base tray for receiving the cells and cell culture media, including a bottom plate and a side wall. The intermediate tray is positioned between the cover and the base tray, such that the gap region of the intermediate tray bottom plate is in alignment with the port located on the cover, resulting in the port, the intermediate tray and the base tray in fluid communication with one another which provides direct access, such as by a user to
(Continued)

remove and/or add cells, cell media, and nutrients located on each of the intermediate and/or the base trays. Alternatively, the cell cultivating flask includes a plurality of intermediate trays stacked on top of one another and the gap regions of each intermediate tray are in alignment with each other and with the port on the cover.

17 Claims, 19 Drawing Sheets

(51) Int. Cl.
*C12M 1/12* (2006.01)
*C12M 3/00* (2006.01)

(52) U.S. Cl.
CPC ............ *C12M 23/34* (2013.01); *C12M 23/38* (2013.01); *C12M 23/58* (2013.01); *C12M 25/06* (2013.01); *C12M 37/02* (2013.01)

(58) Field of Classification Search
USPC ...................................................... 435/294.1
See application file for complete search history.

(56) References Cited

U.S. PATENT DOCUMENTS

| | | | |
|---|---|---|---|
| 5,139,952 A | 8/1992 | Honda et al. | |
| 5,310,676 A | 5/1994 | Johansson et al. | |
| 5,695,987 A | 12/1997 | Kayal et al. | |
| 5,783,440 A * | 7/1998 | Stevens | C12M 23/32 215/386 |
| 6,107,085 A * | 8/2000 | Coughlin et al. | 435/299.1 |
| 6,569,675 B2 * | 5/2003 | Wall et al. | 435/304.2 |
| 2001/0055803 A1 | 12/2001 | Wall et al. | |
| 2002/0045252 A1 | 4/2002 | Yamashita et al. | |
| 2006/0205065 A1 | 9/2006 | Bossi et al. | |
| 2007/0026516 A1 * | 2/2007 | Martin | C12M 23/04 435/297.5 |
| 2007/0065933 A1 | 3/2007 | Esser et al. | |
| 2007/0077655 A1 * | 4/2007 | Unger | C12M 99/00 435/404 |
| 2008/0201083 A1 * | 8/2008 | Hata | G06T 7/0012 702/21 |
| 2009/0148941 A1 * | 6/2009 | Florez et al. | 435/325 |

FOREIGN PATENT DOCUMENTS

| | | | | |
|---|---|---|---|---|
| WO | 98/10055 A1 | | 3/1998 | |
| WO | WO 2006/101056 | * | 9/2006 | ............. C12M 1/34 |
| WO | WO 2008/069902 | | 6/2008 | |
| WO | 2010/008586 A2 | | 1/2010 | |

OTHER PUBLICATIONS

International Preliminary Report on Patentability received for PCT Patent Application No. PCT/US2009/004118, issued on Jan. 16, 2011, 5 pages.

* cited by examiner

LAYERED FLASK CELL CULTURE SYSTEM

CROSS-REFERENCED TO RELATED APPLICATIONS

This application claims the benefit of U.S. Provisional Patent Application No. 61/207,683, filed on Feb. 14, 2009 and of U.S. Provisional Patent Application No. 61/134,985, filed on Jul. 16, 2008, the entire contents of which are incorporated by reference herein.

The present invention relates to a cell culture system having a device or vessel with one or more tiers of cell growth surfaces in fluid communication with one another. More particularly, it relates to a flask system having multiple trays of cell growth surfaces wherein cell growth media on each tray is directly accessible through the same resealable port.

BACKGROUND OF THE INVENTION

Small-scale cell culture devices have existed in the form of shaker flasks and roller bottles for years. More recently, single layer and now multilayered flask bottles have been developed. The current trend in research has demanded more cells to fulfill the high throughput screen campaigns in drug discovery companies. Additionally, the use of cell-based assays are rapidly increasing because of the push to challenge potential drug candidates earlier in the development process. A typical cell based assay or HTS screening run can require from about $10^9$ to about $10^{10}$ cells. A standard single layered flask can deliver about $10^7$ cells. The current cell need requires researchers to maintain and feed 10 to 100 standard flasks in order to reach a requisite number of cells to run a given cell based assay or HTS screening, so new multilayered formats are needed. Thus, it would be desirable to have a cell culture system that provides a high number of cells without a substantial increase in the number of standard flasks to be maintained and fed.

One such product has two trays attached to each other and inserted within a flask to form a three culture layered flask. The flask is generally rectangular with a typical threaded bottle opening at its forward most converging sidewall which is in the form of bottle neck (See U.S. Pat. No. 5,310,676). Each tray has a sidewall around its entire periphery and the sidewalls are sealed to each other. In order to provide cell and liquid access to the middle and lower tray one needs to build a tunnel along the end wall of the trays or flask that liquidly interconnect the trays so that liquid and cells can be flowed into and out of the trays.

Another product uses up to ten trays having each upper surface covered by a gas permeable film. Each tray has a sidewall extending upwardly from the surface. The trays are stacked together and the sidewalls fused to form an integral mass. A manifold and bottle neck sidewall with a typical threaded bottle opening is then bonded to the front end of the trays to complete the flask. (See WO 2008/069902 A3). The manifold provides access to the opened end of the trays.

The systems taught in U.S. Pat. No. 5,310,676 and WO 2008/069902 A3) each have drawbacks. Neither is easily accessible with a pipette or syringe for the addition of fluid or cells, sampling or removal of the cells upon completion of the growth cycle. In fact, the use of a pipette or syringe is restricted because the bottle opening is positioned on the sidewall and the trays are blocking pipette access to the media and the cells. It would be desirable to be able to pipette the media and cells directly from a culture device, using standard pipetting tools and standard cell culture techniques.

Application of cells and liquid is difficult and often incomplete. U.S. Pat. No. 5,310,676 relies upon the molded in tunnel to aid in its distribution which can be difficult and time consuming. Liquid must be added to the flask in an upright position which can lead to foaming and damage to critical proteins in the media. Then the flask is rotated in various directions to ensure that all trays receive an adequate amount of fluid. Likewise, removal of the liquid and/or cells require passage through the tunnel in order to be recovered. Lastly, the number of trays is insufficient to effectively increase the high yields needed by today's scientists.

WO 2008/069902 uses a manifold to distribute liquid and cells into a flask by adding the liquid (containing cells and/or growth media) to the neck portion of the flask. The neck is closed and the flask is shaken tapped, or otherwise moved to dislodge any air that would become trapped within the layers of the system. Lastly as the space between the trays is very small and the gas permeable film forms the upper limit of media on any given tray, the thickness of the media is fixed at about 0.32 mls per $cm^2$. Depending on the cell types being cultured the media needs are different. For example, a human or mouse stem cell is a highly metabolically active cell and demands a high level of media, typically in the range of 0.4 mls per $cm^2$, whereas a slow metabolizing cell line such as CHO, MDCK or fibroblast may only require 0.2 mls per $cm^2$. Since WO 2008/069902 has a fixed media volume to fill the system, the researcher needs to adjust the cell feeding, and maintain a schedule for each cell type being cultured, or else waste expensive media and additives. Additionally, scientists prefer to be able to vary the amount of media they can use in order to optimize the growing conditions, a parameter that WO 2008/069902 does not enable a scientist to optimize. It would be desirable to provide a culture device having layers that easily fill with media without the restriction of tunnels, or the need to dislodge air entrapped within the layers.

As the cells grow, the researcher routinely needs to access the status of growth of the culture so that appropriate steps can be taken, such as when the cells are near confluent the researcher will detach them from the culture tray for use in assays, screens or the like, or to reseed new culture systems to continue to expand the cell line. It is important to recover the cells prior to 100% confluency. These systems typically require the researcher to move the culture system to an expensive microscope that may or may not be in the culture area, to investigate the cell growth status. It would desirable to be able to fill the culture device with the desired amount of media and additives to satisfy the needs of the cell type, as well as the researcher's work schedule. Additionally, it would be desirable to provide a cell culture system that enables visualization of the cells without having to transport the flask or the like housing the cells to an expensive microscope.

Typically, laboratories that are working with high numbers of cells as described, use a variety of automated equipment such as multiwell plate handlers and liquid dispensing systems to increase throughput and reduce data variability due to the operator error. These culture systems can be automated, but are limited to systems equipped with articulating arms that can grasp the system and pour the liquid out into a receiver vessel. Systems with these complex articulating arms are expensive and not available to most laboratories. Therefore, most uses for the above culture systems are limited to a manual operator manipulating the systems, which runs counter to the work practices of high throughput laboratories. Thus, it would be desirable to provide a cell culture system compatible with the automated systems currently in most laboratories, and not require special articulating arms to automate.

SUMMARY OF THE INVENTION

The present invention provides a single or multitier cell culture vessel which is easy to fill, easy to empty, easily accessible by pipette or syringe, and provides high throughput capabilities desired by the industry.

The present invention is based, at least in part, on a multitier cell culture system including a device or vessel such as a flask or the like, including a cover having a top plate, a side wall, typically three or more, and a resealable port; an intermediate tray for receiving a cell culture media, wherein the intermediate tray includes a bottom plate, a side wall, typically three or more, and a gap region formed between an interior upwardly angled lip located on an interior portion of the intermediate tray bottom plate, and an adjacent outwardly angled side wall portion of the intermediate tray bottom plate, wherein the lip has a outwardly swooping curvilinear interior edge feature; and a base tray for receiving the cell culture media, including a bottom plate and a side wall, typically three or more. The intermediate tray is positioned between the cover and the base tray, such that the gap region of the intermediate tray bottom plate is in alignment with the port located on the cover, resulting in the port, the intermediate tray and the base tray in fluid communication with one another, which provides access, such as by a user, directly to the cell media and cells located on each of the intermediate tray and the base trays.

According to another embodiment, the present invention is based, at least in part, on a multitier cell cultivating vessel or device, such as a flask including a cover having a top plate, a side wall, typically three or more, and a resealable port; a plurality of intermediate trays stacked on top of one another for receiving a cell culture media, each tray having a bottom plate having an underside, an upperside, a side wall, typically three or more, and a gap region formed between an interior upwardly angled lip having a swooping curvilinear edge located on an interior portion of the bottom plate and an adjacent outwardly angled side wall portion of the bottom plate; and a base tray for receiving a cell culture media having a bottom plate and a side wall, typically three or more. The plurality of intermediate trays are positioned between the cover and the base tray, and the gap regions of each intermediate tray are in alignment with each other, and with the port on the cover, resulting in the port, the stacked plurality of intermediate trays and the base tray in fluid communication with one another providing direct access to the cells and cell media located on each of the intermediate and base trays.

According to another embodiment, the present invention is based, at least in part, on a cell cultivating vessel or device, such as a flask having a bottom and a top wall joined together by one or more sidewalls, typically three or more, which are substantially perpendicular to the top and bottom walls. The top has a threaded opening on to which a vented cap is threadably mated, wherein the top wall is preferably substantially planar. An interior space is defined by the walls. The bottom wall has at least two portions, preferably three; a first portion in one plane, a second portion in a second plane above, and preferably parallel, to the plane of the first portion and an interconnecting portion which is at an angle to interconnect the first portion to the second portion.

In some embodiments, the interconnecting portion is incorporated into the second portion such that the area of the second portion adjacent the first portion is in the plane of the first portion and the area of the second portion beyond that is at an upward angle away from the first plane to a desired point or second plane. The bottom walls extend out from the outside bottom planar surface to form a perimeter skirt. The perimeter skirt forms a linear transition to the end wall. The linear skirt transition creates an angle such that when the cell culture system is in position, the linear transitional skirt lies flat onto a work surface such that all the internal plane portions (one, two, three and four) are positioned at a positive angle such that liquid on those surfaces will drain towards the access port end of the culture system. This feature enables full recovery of spent media during media changes and complete recovery of the cells post culture. Trays are placed in the interior space, preferably only in the area defined by the first portion of the bottom wall and a portion of the interconnecting portion if used.

One object of the present invention is to provide a multitier cell culture device that permits a user to pipette the cell media and cells directly from the device, using standard pipette tools and standard cell culture techniques.

It is another object of the present invention to provide a cell culture system that provides a high number of cells without an increase in the number of standard flasks to be maintained and fed.

Another object of the present invention to provide a cell culture system compatible with the automated systems currently used in most laboratories, and not require special articulating arms to automate.

A further object of the present invention to provide a cell culture system that provides a multitier cell culture device wherein each tier or tray easily fills with media without the restriction of tunnels, or the need to dislodge air entrapped within the separate levels.

Another object of the present invention to provide a multitier cell culture system that provides a cell culture device that can be easily filled or emptied with the desired amount of media, additives and cells to satisfy the needs of the cell type, as well as a researcher's work schedule.

It is another object of the present invention to provide a cell culture system that provides visualization of the cells within the culture device without having to transport the flask or device housing the cells to an expensive microscope or other type of optical viewing instrument.

Additional features and advantages of the invention will be set forth in the detailed description which follows. Many modifications and variations of this invention can be made without departing from its spirit and scope, as will be apparent to those skilled in the art. It is to be understood that both the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

IN THE DRAWINGS

FIGS. 5A-E shows a top down cross-sectional view of various sidewall embodiments according to the present invention.

Figure 6A:
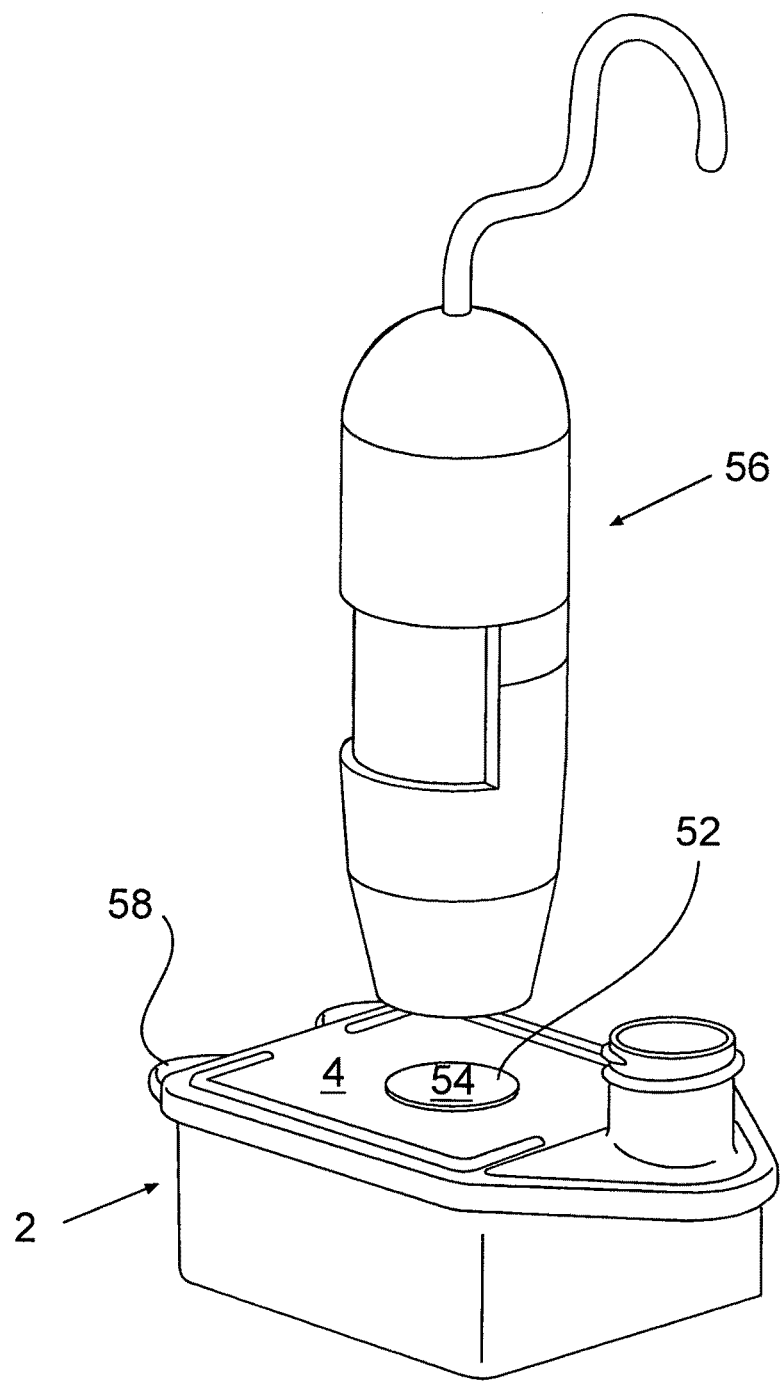
Figure 6B:
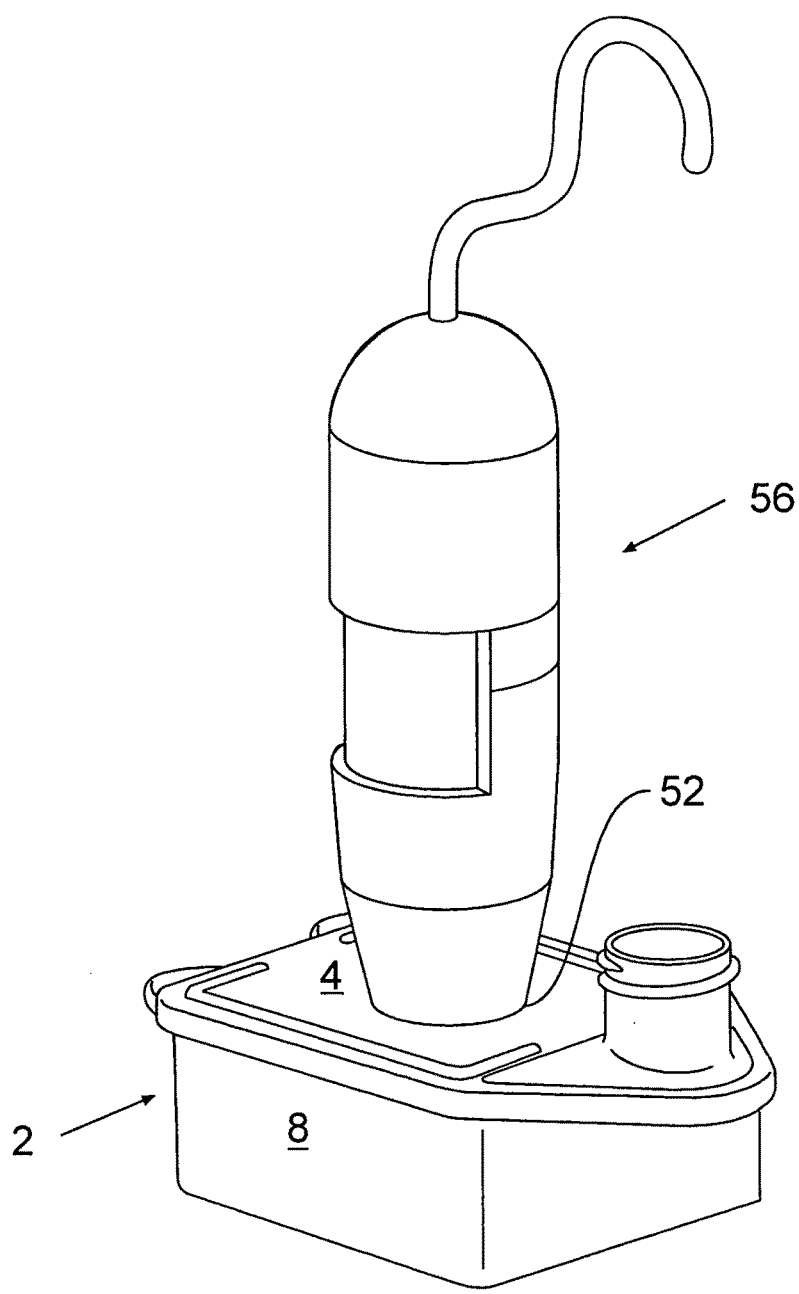

FIGS. 6A-6B show perspective views of an additional embodiment of the present invention.

Figure 7:
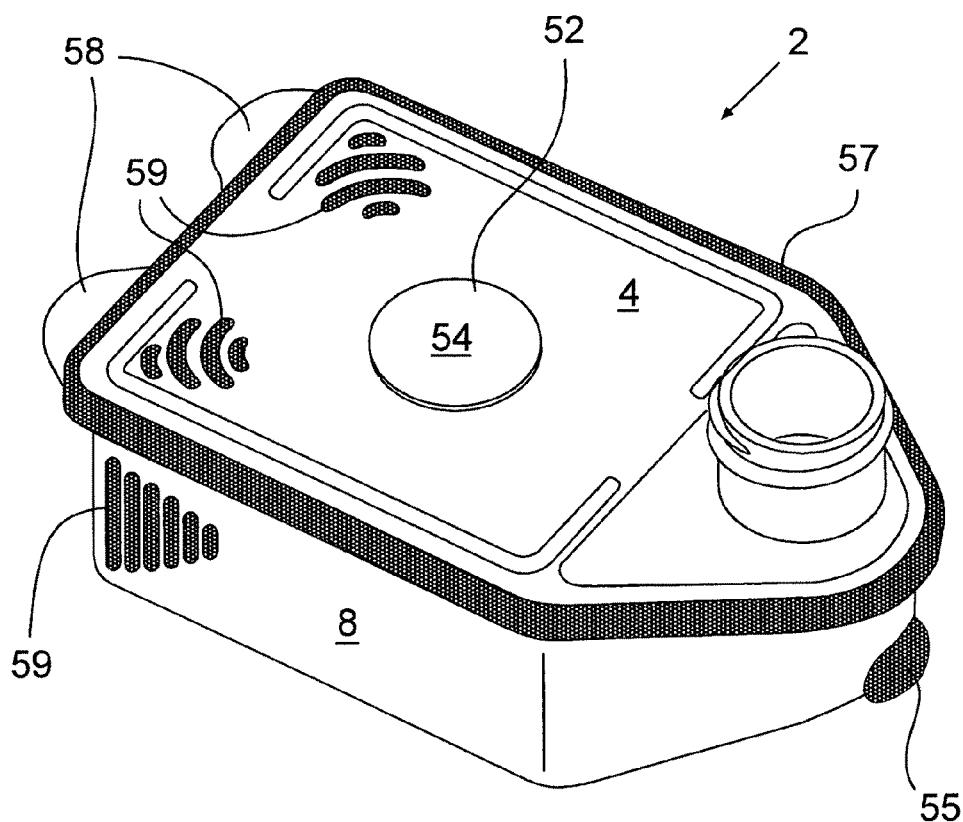

FIG. 7 shows a perspective view of an additional embodiment of the present invention.

Figure 8:
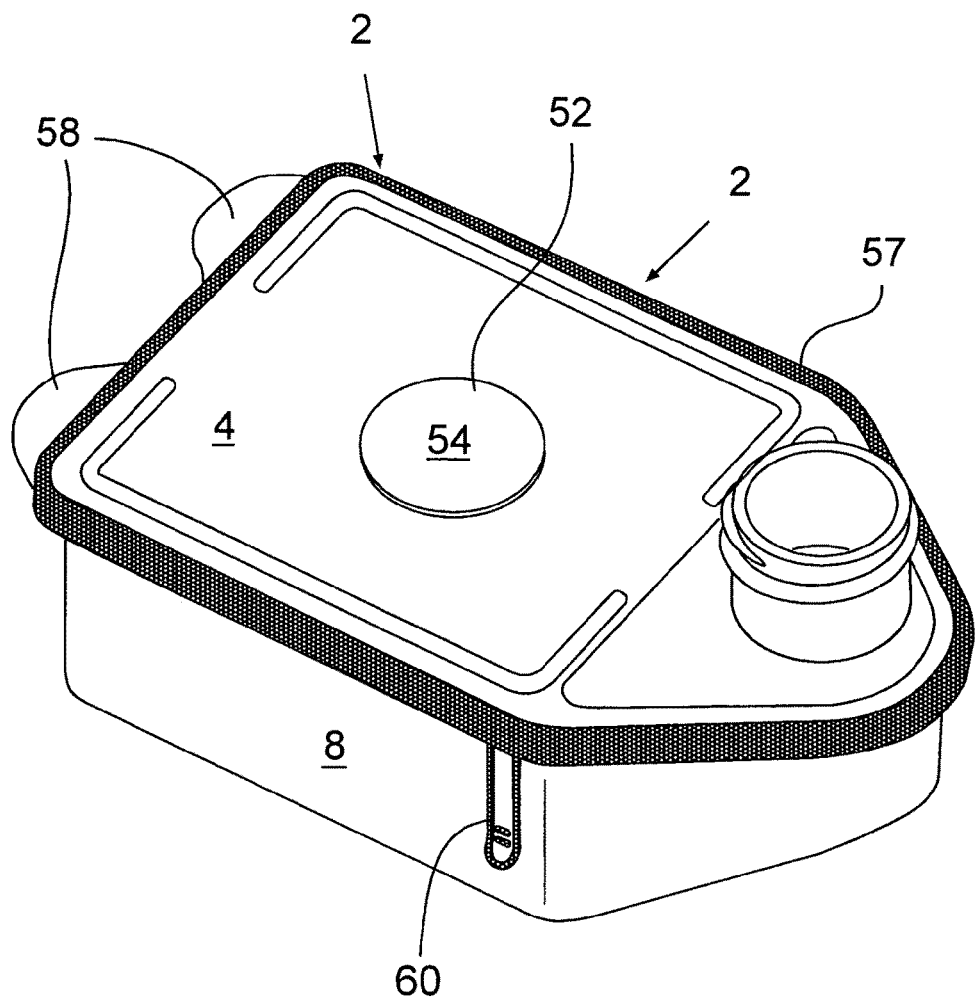

FIG. 8 shows another perspective view of an additional embodiment of the present invention.

Figure 9:
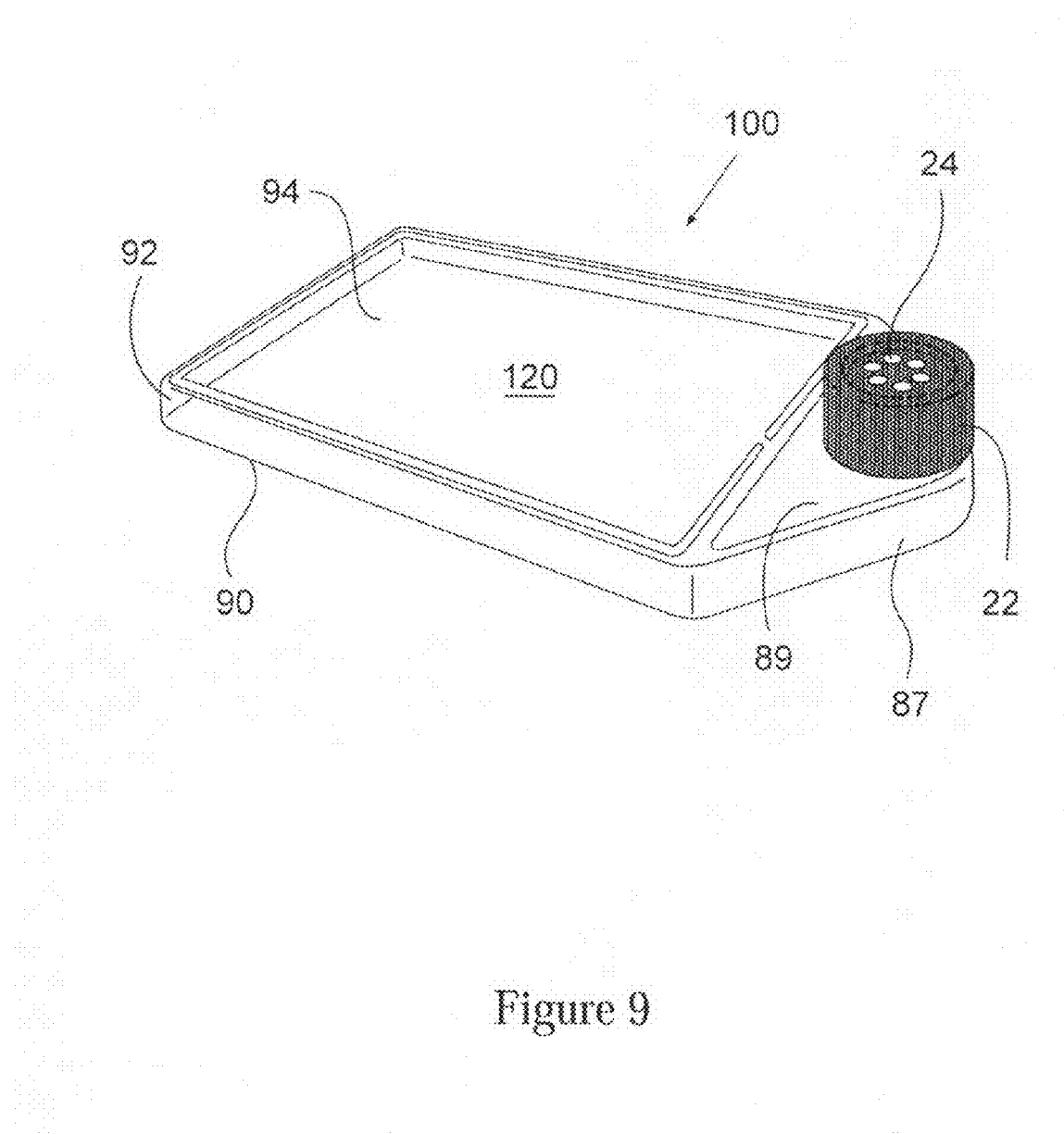

FIG. 9 shows a perspective view of an additional embodiment of the present invention.

Figure 10:
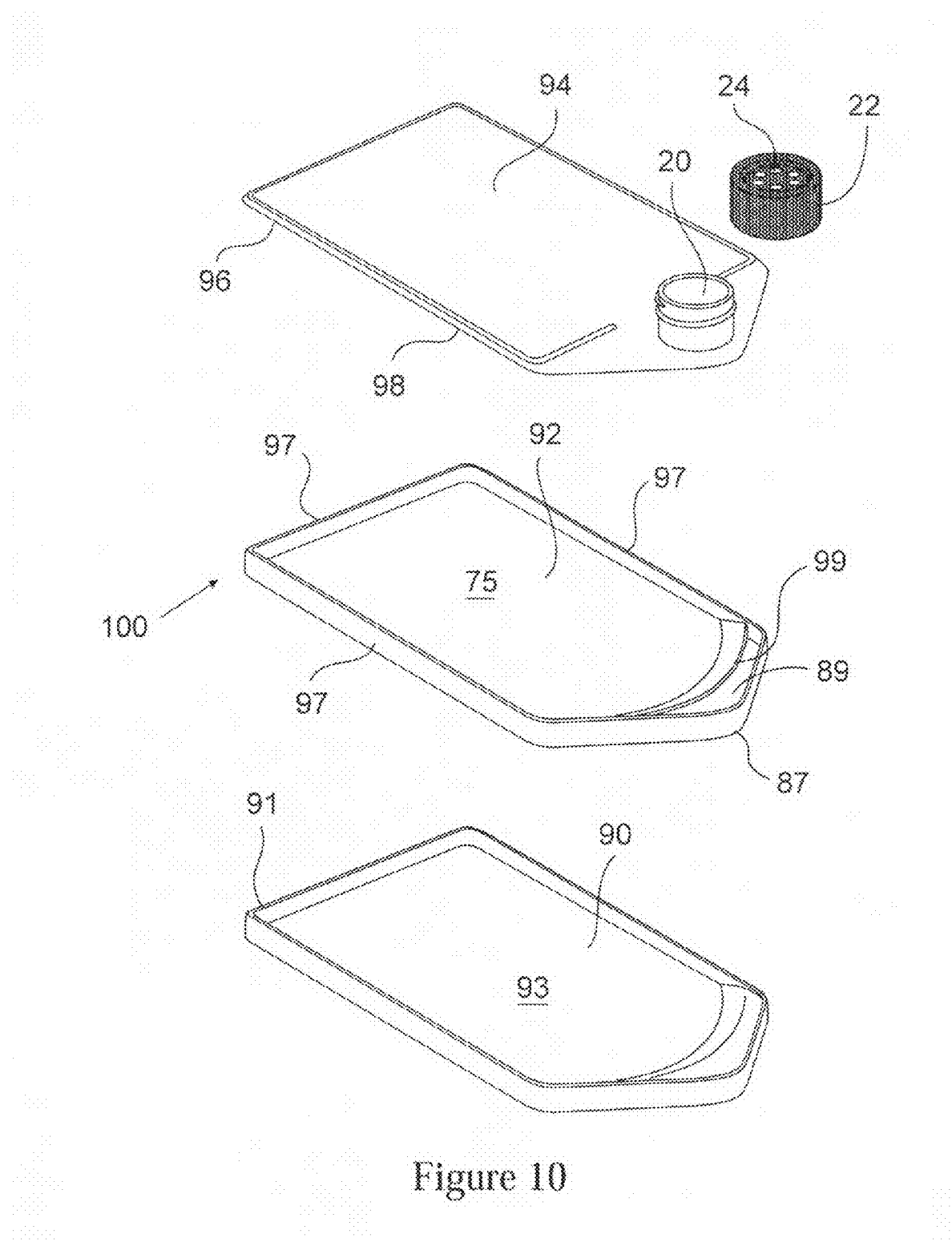

FIG. 10 shows a perspective view of the individual components of the embodiment in FIG. 10.

Figure 11:
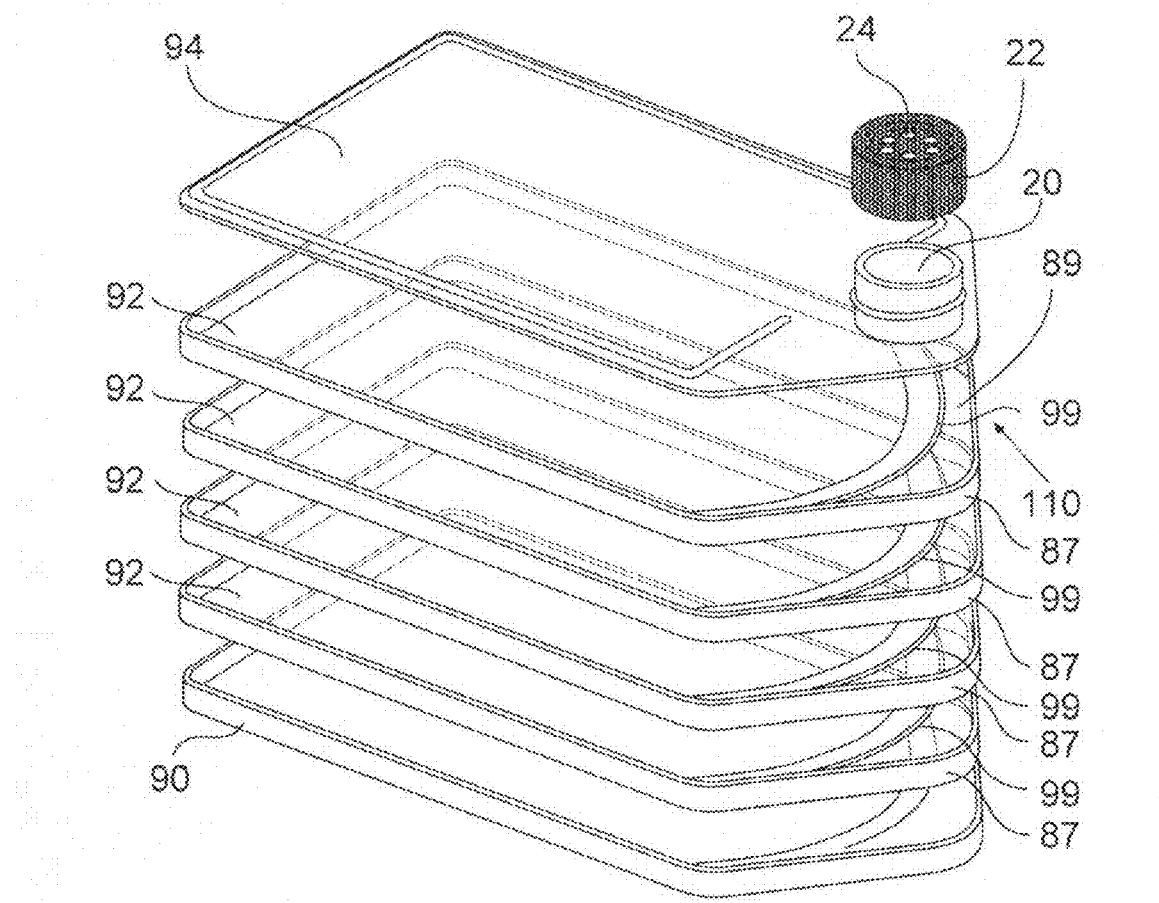

FIG. 11 shows an exploded view of an additional embodiment of the present invention depicted in FIG. 10.

Figure 12A:
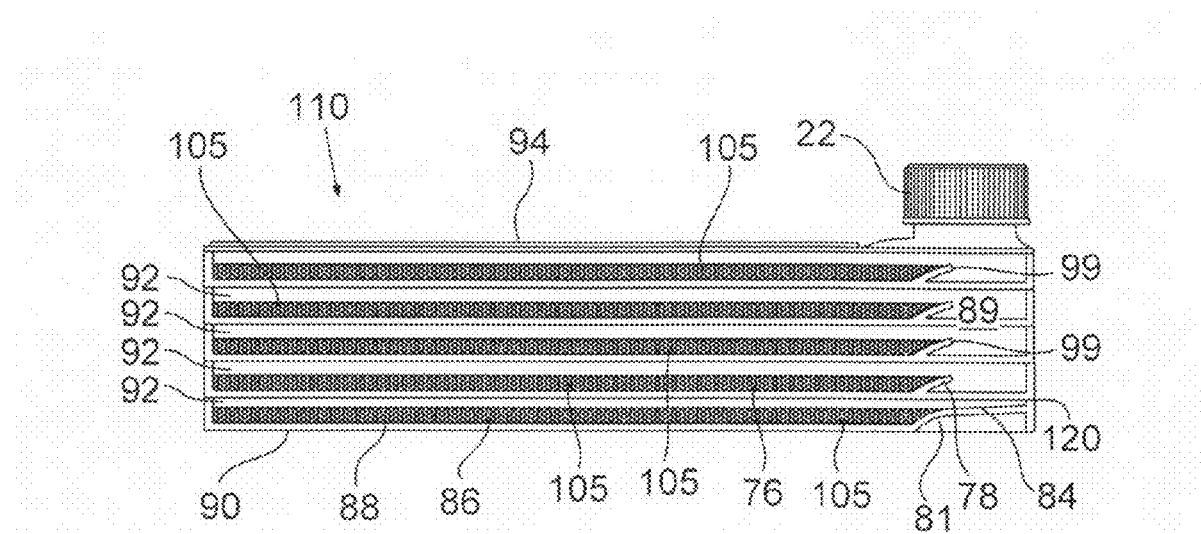

FIG. 12a shows a side view of the embodiment of the present invention depicted in FIG. 11.

Figure 12B:
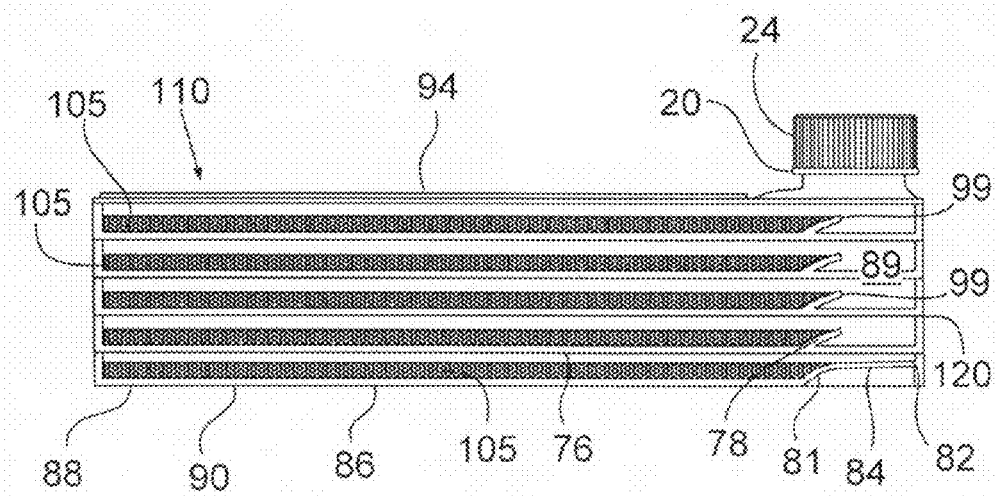

FIG. 12b shows a cross-sectional view of the embodiment of the present invention depicted in FIG. 11.

Figure 13:
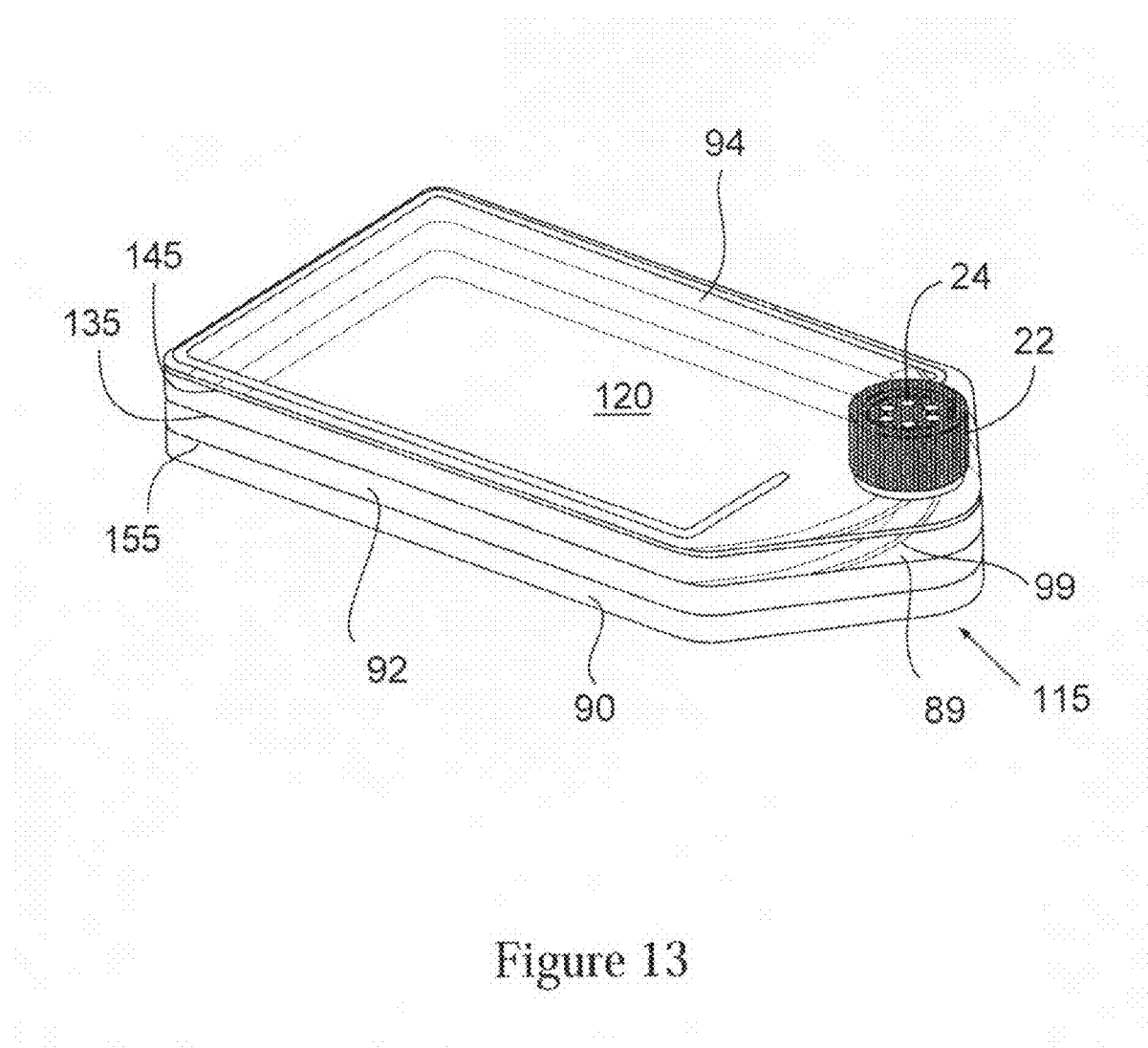

FIG. 13 shows a perspective view of an additional embodiment of the present invention.

Figure 14:
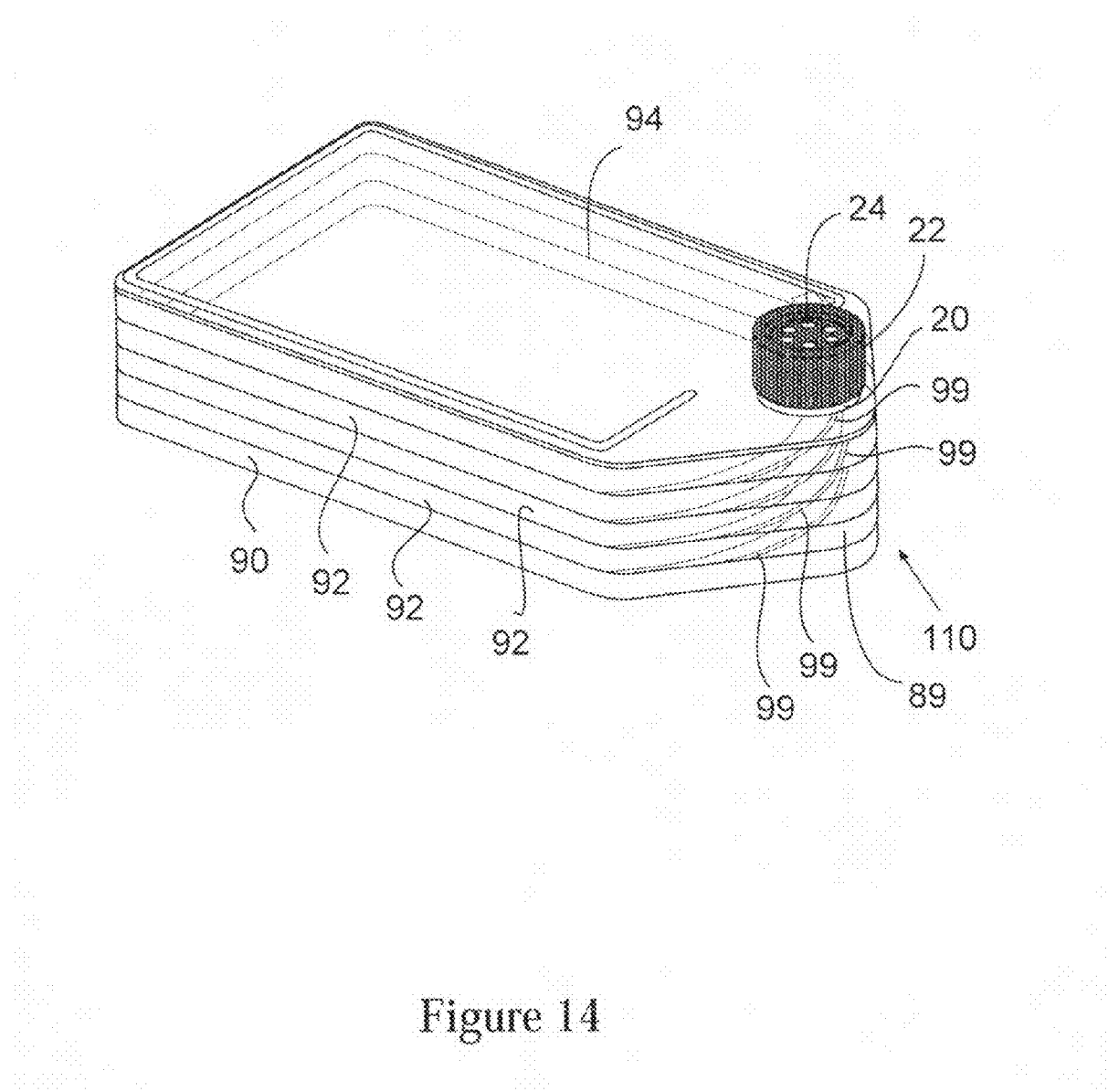

FIG. 14 shows a perspective view of an additional embodiment of the present invention.

Figure 15:
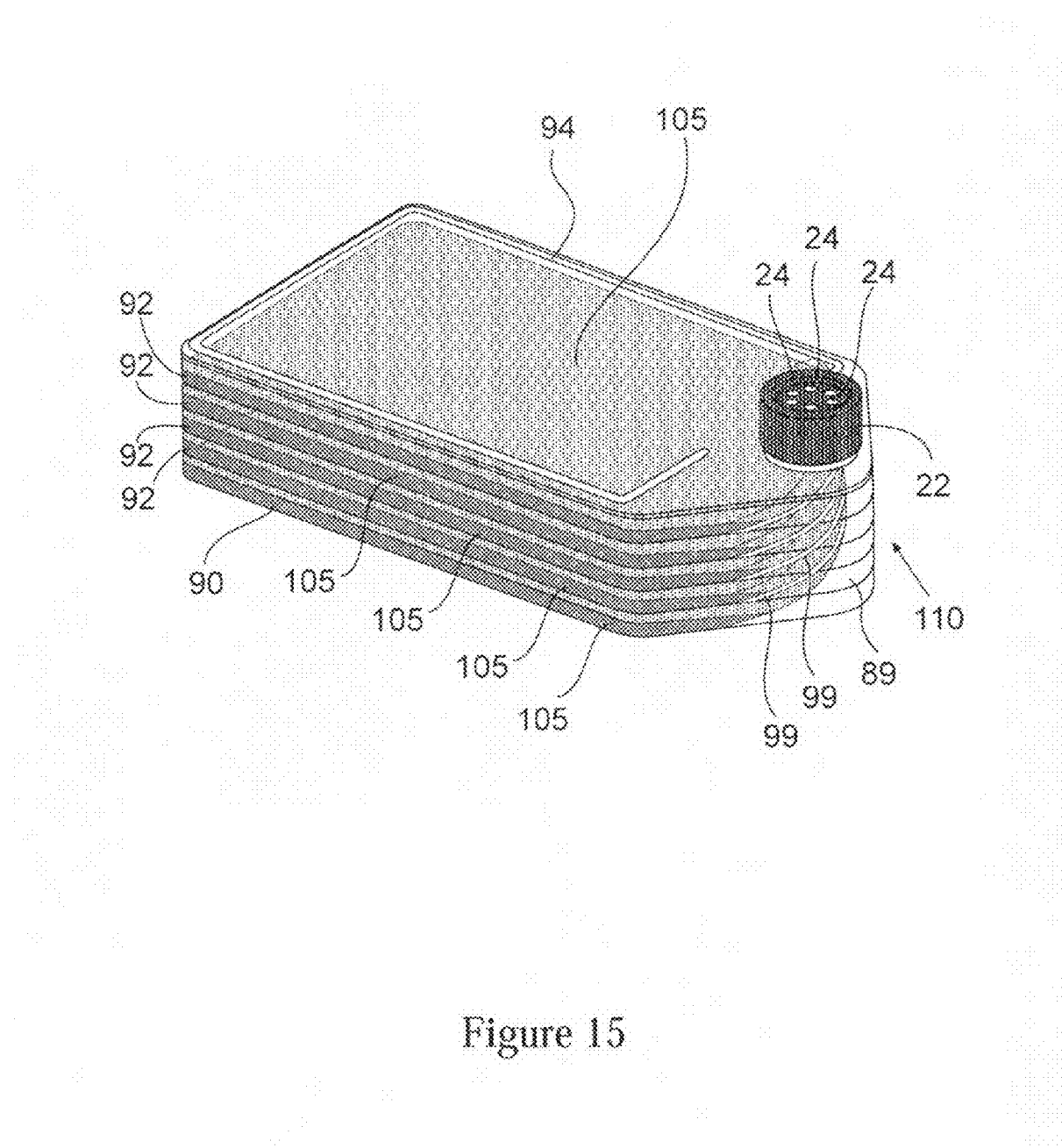

FIG. 15 shows a perspective view of an additional embodiment of the present invention filled with cell culture media.

Figure 16A:
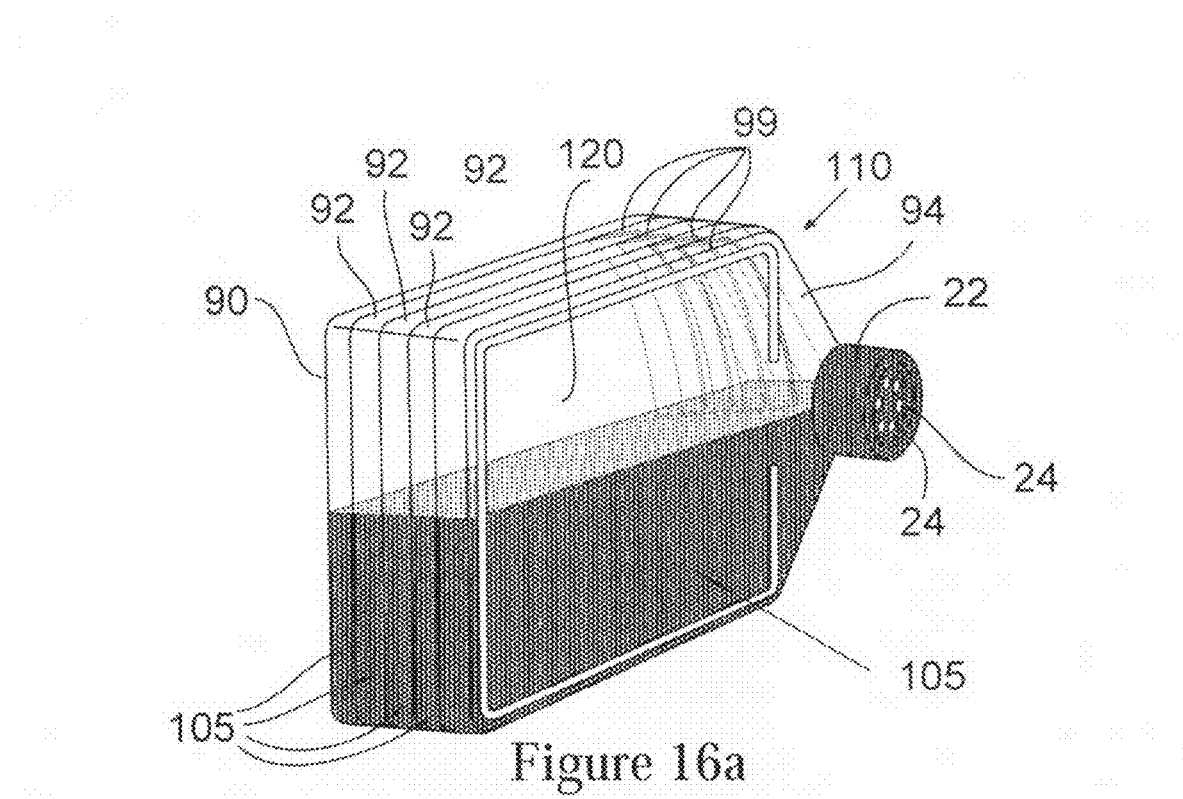

FIG. 16a shows a perspective view of an additional embodiment of the present invention containing cell culture media equally filling the trays.

Figure 16B:
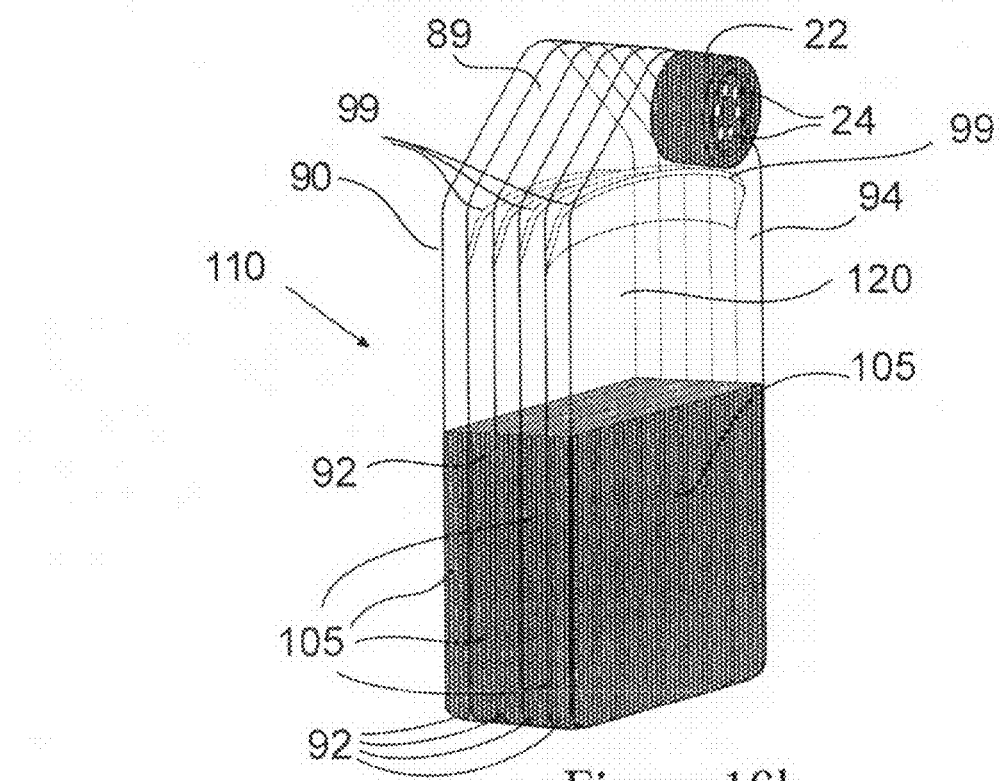

FIG. 16b shows a perspective view of the present invention depicted in FIG. 15 in a tipped position in order to spread the cell culture media throughout the trays.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

As used herein, the singular forms "a," "an," and "the" include plural referents unless the context clearly dictates otherwise.

Figure 1:
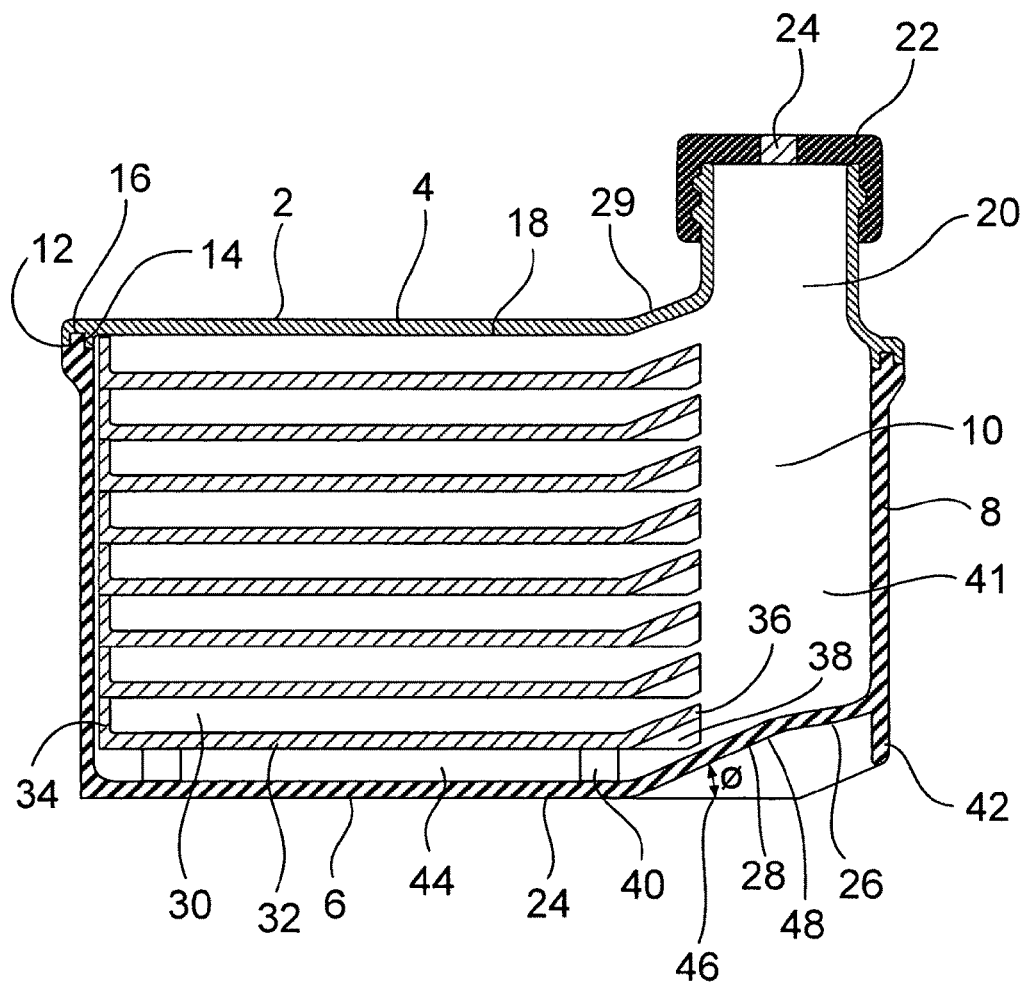
FIG. 1 shows a cross-sectional view of a first embodiment of the present invention.

FIG. 1 shows an embodiment of the present invention, wherein flask 2 preferably comprises a transparent, translucent or nontransparent glass or plastic material. The flask 2 has a top wall 4, a bottom wall 6 and three or more sidewalls 8 which extend substantially perpendicular to and between the top wall 4 and the bottom wall 6 to define an interior space 10. As shown the bottom wall 6 and sidewalls 8 are formed as one piece. They may if desired be formed of individual pieces if desired. Top wall 4 is liquid tightly sealed to the upper edge 12 of the sidewalls 8 such as by heat bonding, melt bonding, sonic vibration welding or adhesives. Optionally as in this embodiment, the upper edge 12 of the sidewalls has a feature, in this case a ridge 14 that mates with a corresponding feature in this case a trough 16 in the bottom or inner surface 18 of the top wall 4 so that the walls are properly aligned and sealed together. If the top wall is desired to be removal the top wall 4 can be secured to the sidewalls 8 by other well-known means such as screws, clamps, sliding dovetails and the like (not shown).

The top wall 4 has a port 20 that can be selectively opened and closed. One such means for selectively opening and closing the port 20 is a cap 22 which can and preferably has a vent 24 that allows for the transfer of gases into and out of the interior 10 without contamination. This can be accomplished by using a frit, metal such as stainless steel or plastic such as a POREX® frit or a hydrophobic membrane or filter, all of which have a pore size designed to keep out bacteria, dust and other such contaminants. A typical pore size used in such a frit or filter or membrane is less than about 0.65 micron, preferably less than about 0.4 micron and more preferably about 0.22 micron.

As shown the bottom wall 6 in this embodiment has a first substantially flat portion 24 and a second substantially portion 26 connected to each other by a substantially planar interconnecting portion 28 that is on an angle so as to connect the two portions 24 and 26 together. The first portion 24 is at one desired horizontal plane that is below that second horizontal plane of the second portion 26. This means that when in its use position as shown in FIG. 1, the first portion 24 is the lowermost portion of the interior 10 of the device 2.

A portion of the interior 10 contains one or more cell growing trays 30. These trays have a substantially flat bottom 32 and sidewalls 34 that run around the periphery of the tray 30. The number of sidewalls 34 of the tray(s) 30 is equal in number to the number of sidewalls of the flask 2. The front sidewall 36 of the tray(s) is different than the rest of the sidewalls 34 of the tray(s) 30 in that it is at upward angle away from the substantially flat bottom 32 of each tray 30. The front sidewall 36 or lip provides open access to each tray for cells, liquids and gases when they 30 are arranged within the flask 2. Also shown on each tray 30 is an optional feature 38 which is a foot that extends outwardly from the front sidewall 36 of each tray 30.

The bottom walls extend a distance from the outside bottom planar surface to form a perimeter skirt. The perimeter skirt forms a linear transition to the end wall. The linear skirt transition creates an angle that when the culture system is in position the transitional skirt flat onto a work surface all the internal plane portions (one, two, three and four) are positioned at a positive angle so that liquid on those surfaces will drain toward the access port end of the culture system.

The feature enables full recovery of spent media during media changes and complete recovery of the cells post culture.

The tray(s) 30 are spaced about the bottom wall 6 of the flask 2 so that the inner surface 44 of the bottom wall acts as a tray. In this embodiment the tray(s) are spaced from the bottom surface 44 by detents formed on the opposite sidewalls 8. These detents or rests extend outwardly into the interior 10 to an extent sufficient to support the tray(s) in the interior 10. Typically they can extend outwardly from the sidewalls into the space by a distance of from about 3 mm to about 7 mm. Alternatively, the bottommost tray 30 may have feet (not shown) formed on its bottom surface 32 to provide the necessary spacing with the inner bottom surface 44 of the interior 10. In another embodiment if the bottom surface 44 is not desired as a cell growth layer, no detent or feet are needed and the tray(s) bottom 32 may contact the bottom surface 44.

Preferably, the tray(s) 30 are simply stacked onto of each other and retained in the flask by the spacing considerations, making them narrow enough so that the tray(s) 30 once inserted cannot disassociate from each other. Optionally, they may be sealed to each other such as by the use of adhesives or heat bonding and the like, or they may have a strap such as one or more tie wraps or cable wraps (not shown) placed around them, or they may contain sliding dovetails or snap fits (not shown) between their adjacent surfaces to hold them together.

Figure 2A:
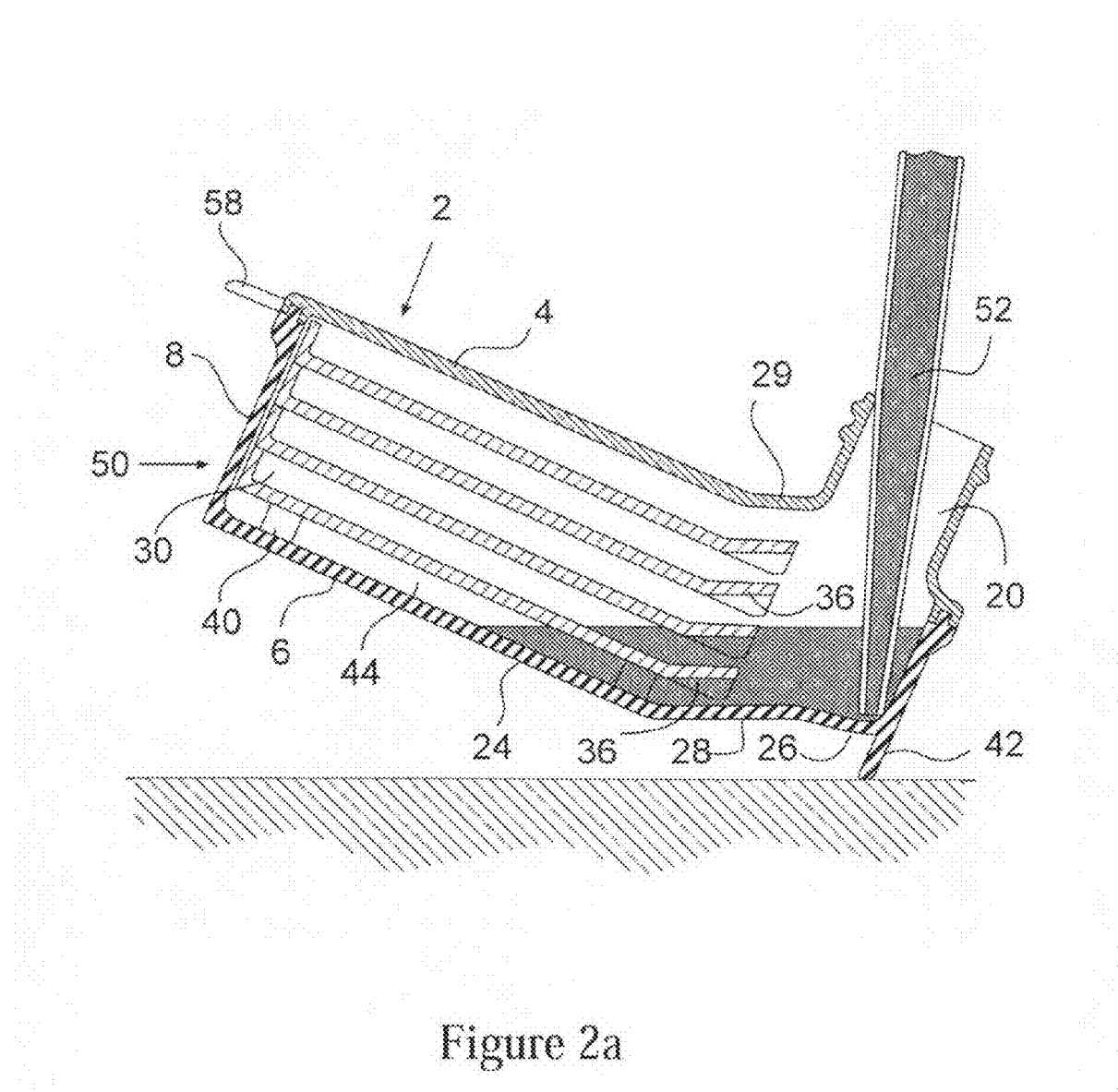
FIGS. 2a and 2b show cross-sectional views of an additional embodiment of the present invention.
Figure 2B:
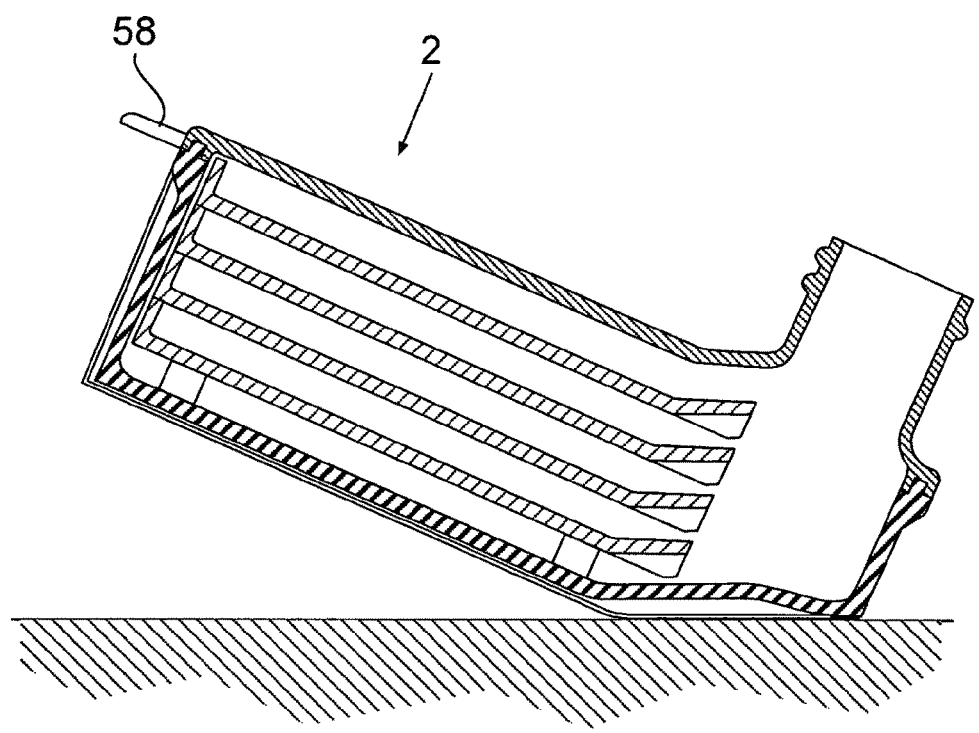

The angle of the interconnecting portion 28 is equal to or greater than the angle of the front sidewall 36 of each tray 30 so that when moved to its loading/unloading position as described in FIG. 2 the liquid and cells can flow to their appropriate locations. Typically, the angle of the interconnecting portion 28 is from about 10 degrees to about 60 degrees as measured by the angle alpha 46 between the first plane of the first portion 24 and the outer bottom surface 48 of the interconnecting portion 28. Preferably the angle alpha 46 is between about 10 degrees and about 45 degrees, more preferably from about 15 degrees to about 30 degrees and most preferably about 22 degrees. The angle of the front sidewall 36 as described above is equal the angle alpha 46 or less than the angle alpha 46 but preferably is never greater than the angle alpha 46. Additionally, top wall 4 may optionally have a similar third portion 29 (as shown) that corresponds to the angle alpha in a position directly above the interface between the first portion 24 and the interconnecting portion 28 of the bottom wall 6. This is a preferred option so that the space between the top tray and the inner surface of the top wall 4 is the same as the space between any other tray (if more than one is used) and the adjacent surface above it (the bottom surface of the try above it for example). Alternatively the top wall 4 may be substantially planar across its length and the space between the top tray and the top wall can be suitably enlarged if necessary to provide suitable flow of liquids and gases into that tray (not shown).

The tray(s) 30 are contained within the interior 10 to the area circumscribed by the first portion 24 and preferably at least a portion of the interconnecting portion 28 of the bottom wall 6. This leaves an open area 41 in the interior 10 around and adjacent to the port 20 for the entrance and exit of liquids, cells and gases. In the embodiment where the tray(s) 30 are not bonded or otherwise secured to the bottom or sidewalls 6,8 of the flask 2, foot 38 acts as a means for preventing the tray(s) from moving into the open area 41 when the flask is tilted for unloading or if desired for loading as well.

FIG. 2 shows the flask 2 when in its unloading position. This may also be the loading position is desired. As shown, the flask 2 is lifted at its rear 50 and tilted forward on its foot 42 that extends downwardly from the sidewall 8 adjacent the port 20. A pipette or syringe or funnel (pipette 52 is shown) can be inserted into the port 20 and have access to the open area 41 of the interior 10. The second portion 26 when in the unloading optionally loading position becomes the low point of the flask 2. This allows one to easily recover cells or exchange media or add new media or cells into the open area 41 without disturbing the tray(s) or requiring one to tip the flask vertically as is required by the prior art.

Figure 3:
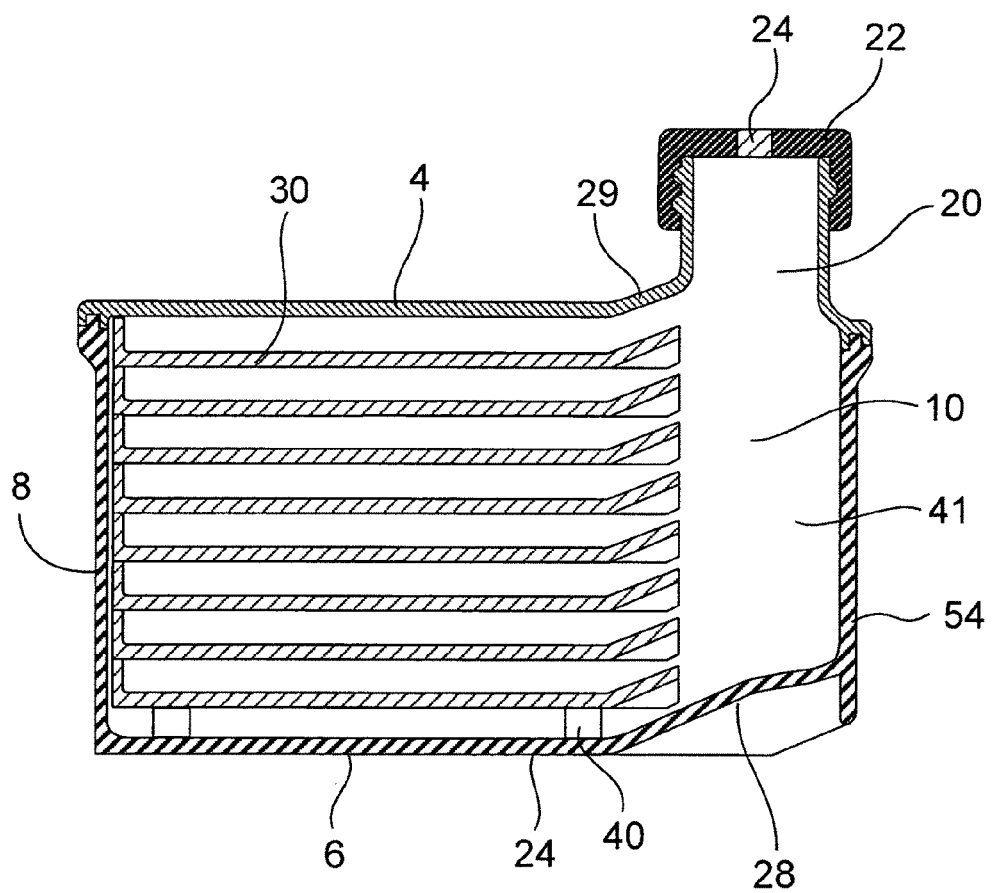
FIG. 3 shows a cross-sectional view of first embodiment of FIG. 1 in the unloading position of the present invention.

FIG. 3 shows an alternative embodiment of the design of FIGS. 1 and 2. In this embodiment, the second portion becomes a part of the interconnecting portion 28 such that there is a flat first portion of the bottom 6 and only an angled interconnecting potion 28 that meets and terminates in the front sidewall 54. The second portion 26 in effect becomes the point at which the interconnecting portion 28 meets the front sidewall 54. The device 2 is used the same way as described as in FIG. 2. All elements common to FIGS. 1 and 3 retain the same reference numbers, perform the same functions, and have the same attributes as described in reference to the embodiment of FIG. 1.

Figure 4:
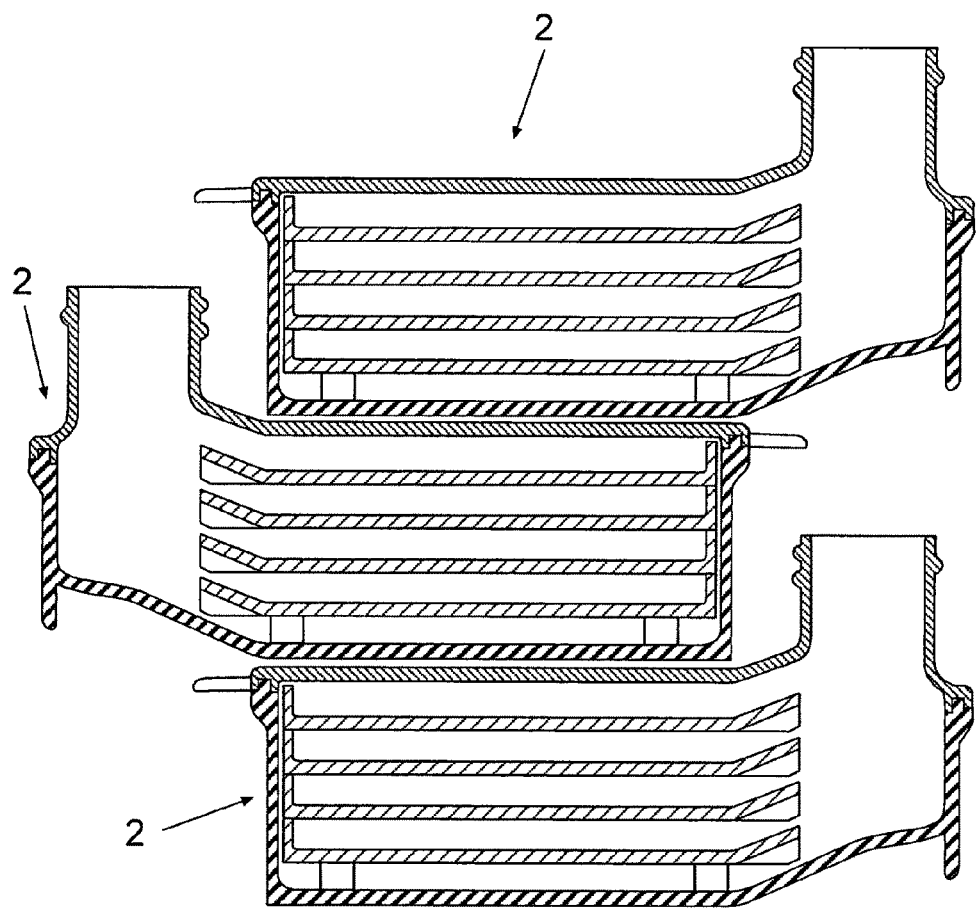
FIG. 4 shows a cross-sectional view of a series of first embodiments of the present invention in stacked formation.

FIG. 4 shows a series of flasks 2 according to the present invention. Due to their design with the relatively flat bottom portions 24 and top wall 4 they can be alternately stacked on top of each other to save floor or hood space during incubation and growth.

Figure 5A:
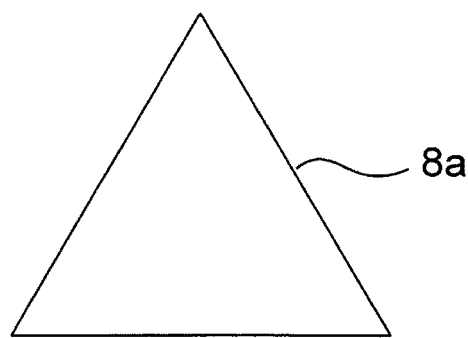
Figure 5B:
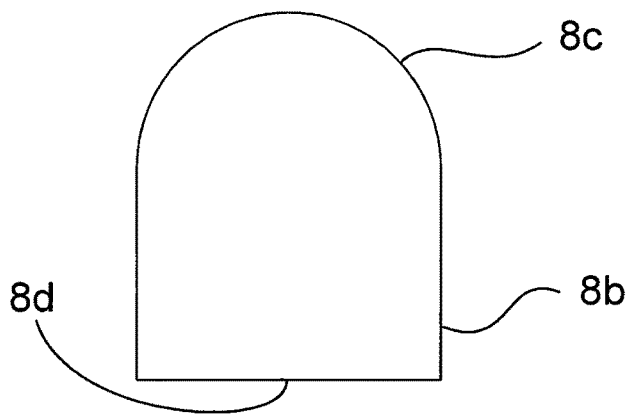
Figure 5C:
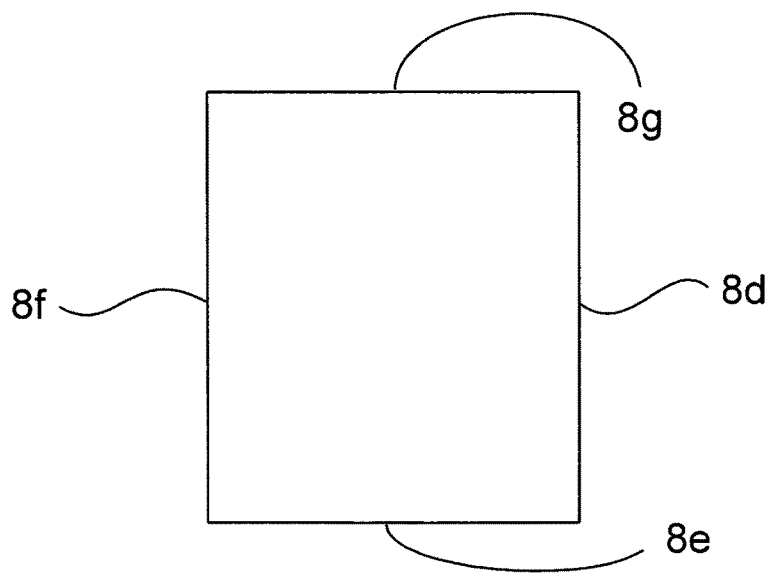
Figure 5D:
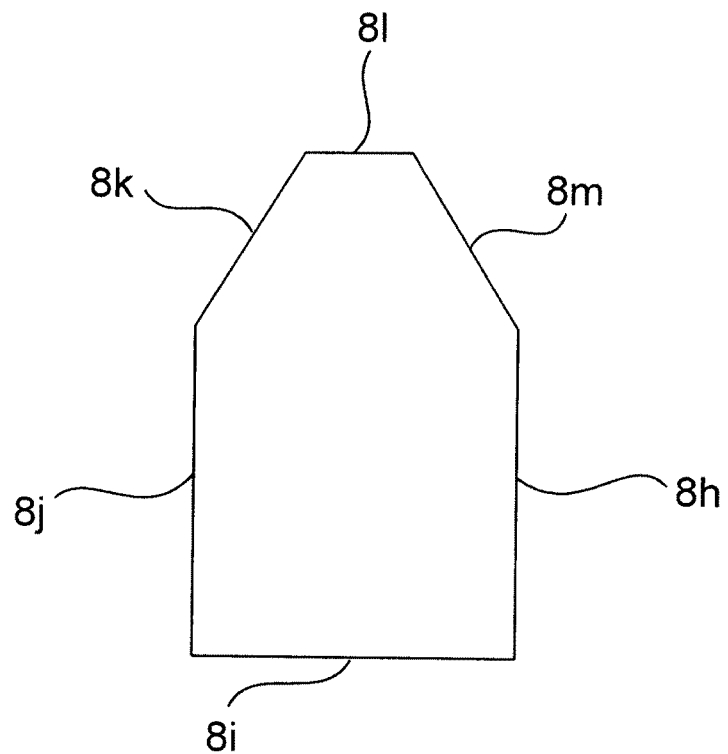
Figure 5E:
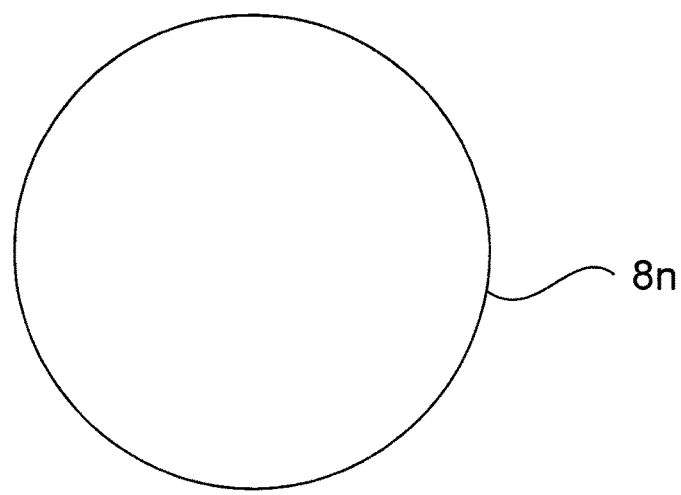

As previously described the flask may have three or more sidewalls 8. FIGS. 5A-D show three different sidewall embodiments of the flask 2 to illustrate this feature. FIG. 5A shows a triangular-shaped flask 2 having three sidewalls 8A. FIG. 5B shows a polygonal sidewall configuration of four more sidewalls with sidewalls 8B and 8D being linear or straight sidewalls and sidewalls 8C being angle or tapered or curved sidewalls. Sidewalls 8c may be an extension of sidewalls 8B in which case there are 3 sidewalls or they may be separate sidewall portions in which the flask has 5 sidewalls in this embodiment. FIG. 5C shows a rectangular-shaped design with four sidewalls 8D-8G. FIG. 5D shows another design with five sidewalls 8I-8M. FIG. 5E shows a single circular sidewall 8N.

The culture system of the invention, when in use, includes a flask filled and/or emptied by a pipette, syringe or similar device, having the culture system positioned on a work surface and having the threaded opening in an upward position. The researcher dispenses the media and cells into the system. The media amount can vary depending on the cell type being cultured, i.e., more media for highly metabolic cells such as stem cells. The researcher seals the system with a gas permeable closure, such as a threaded cap with a hydrophobic bacterial retentive microporous matrix enabling free exchange of gas from outside of the system to the inside. The culture system is tipped to its side, so that the media freely fills the layers insuring a uniform amount between each tray. The system is tipped on to the side wall opposite the closure then tipped forward, resulting in the culture system seated with the first and third portion surfaces substantially planar to the work surface. In this position the media and cells spread uniformly across each culture layer and the first portion surface. This readied culture system is typically placed into an environmental controlled chamber, incubation, for the cell growth phase.

The researcher needs to periodically investigate the status of the culture during the growth phase. This activity typically consists of the culture system being removed from the incubator and transported to a microscope that may or may not be in close proximity. In one embodiment, as shown in FIGS. 6A and 6B, flask 2 additionally includes a lens 54 that be may be molded in the top wall or the bottom walls (not shown) with the focal surface being the first adjacent culture layer. Ideally, the magnification from this lens is 10× to 40× for low level viewing of the cell culture. Preferably, the magnification is 25× to 40× so that visualization of cell growth status and cell detachment during cell recovery is visible with the naked eye. Additionally, a camera system 56 such as the Dino-Lite system (BigC.com Corp., Torrance, Ca) can be secured via a coupling mechanism or mounting system 52 to the top wall 4 or the bottom wall (not shown) to provide image capture. Ideally, this configuration is maintained within the incubator such that monitoring can occur without a researcher having to enter the incubator and disrupt the growth phase of the cells. Additionally, the use of a wireless connection permits the remote monitoring of the cell culture. (not shown)

In another embodiment, as shown in FIG. 7, flask 2 may also include one or more of the following features a) an overmolded seal plastic seal 57 around the perimeter of the flask; b) a non-skid, preferably plastic, button 55 to secure the flask 2 from slipping during the recovery of spent media, cell post cultures or the like when the flask is tipped; c) overmolded plastic ribs or other such feature that provides a user with a non-slip gripping or handling surface. In a preferred embodiment, the plastic used to make these features comprises a thermoplastic elastomer (TPE) with a hard durometer greater than 49 shore A in order to provide the user an appropriate tactile feel for gripping or otherwise handling the flask.

In another alternative embodiment, as shown in FIG. 8, flask 2 may also include an easy to open tear-away element 60 or the like in one of the sidewalls 8, wherein the easy to open tear-away element 60 is preferably a component of the overmolded seal 57.

In another alternative embodiment, as shown in FIGS. 9 and 11, a multitier cell cultivating multitier flask 100 comprising a cover 94 including a top plate 98, side walls 96 and a resealable port 20; an intermediate tray 92 for receiving cells and a cell culture media 105, the intermediate tray having a bottom plate 95, side walls 97, and a gap region 89 formed between an interior upwardly angled lip 78 having a swooping curvilinear interior edge 99 located on an interior portion of the bottom plate and an adjacent outwardly angled side wall 87 of the bottom plate; and a base tray 90 for receiving cells and a cell culture media, including a bottom plate 93 and side walls 91, wherein the tray is positioned between the cover and the base tray, such that the gap region of the bottom plate of the tray is in alignment with the port located on the cover, resulting in the cover, the tray and the base tray in fluid communication with one another which enables a user to directly access each of the cell media located on the tray and the base tray.

In another alternative embodiment as depicted in FIGS. 9 to 16, a cell cultivating flask 100 includes a cover 94 having a top plate 98, one or more side walls 96 and a resealable port 20; a plurality of intermediate trays 92 for receiving cells and a cell culture media 105, each intermediate tray 92 having a bottom plate 95, one or more side walls 97, and a gap region 89 formed between an interior upwardly angled lip 78 having a swooping curvilinear interior edge 99 located on an interior portion of the bottom plate and an adjacent outwardly angled side wall 87 of the bottom plate; and a base tray 90 for receiving cells and a cell culture media, having a bottom plate 93 and one or more side walls 91. The plurality of intermediate trays 92 are positioned between the cover 94 and the base tray 90, such that the plurality of intermediate trays are stacked on top of one another, and the gap regions of the bottom plates 95 of each intermediate tray are in alignment with each other and with the port located on the cover, resulting in the port, the plurality of intermediate trays and the base tray in fluid communication with one another which enables a user to directly access each of the cell media located on the plurality of intermediate trays and base tray, with a standard pipetting device and the like.

As shown in FIG. 13, the side walls 97 on each intermediate tray 92 stacked on top of one another are preferably fused to form a liquid tight seal 135, to the underside of the side walls 97 on next adjoining intermediate tray. In one embodiment, the side walls on each intermediate tray stacked on top of one another are ultrasonically welded 135 to the underside of the side walls of the next adjoining intermediate tray 92; the side wall of the intermediate tray 92 adjacent the cover 94 is ultrasonically welded 145 to the underside of the side wall of the cover 94, and the side wall of the base tray 90 is ultrasonically welded 155 to the underside of the side wall of the adjoining intermediate tray 92.

The resealable port 20 can be selectively opened and closed. One such means for selectively opening and closing the port 20 is a cap 22, which can be threaded and preferably has a vent 24 that allows for the transfer of gases into and out of the interior 10 without contamination. This can be accomplished by using a frit, metal such as stainless steel or plastic such as a POREX® frit or a hydrophobic membrane or filter, all of which have a pore size designed to keep out bacteria, dust and other such contaminants. A typical pore size used in such a frit or filter or membrane is less than about 0.65 micron, preferably less than about 0.4 micron and more preferably about 0.22 micron.

In another alternative embodiment, as shown in FIGS. 9 to 16, a multitier cell cultivating flask 100, 110, 115 includes a bottom wall 88 of a base plate 90 having a first substantially flat portion 86 and a second substantially flat portion 84 connected to each other by a substantially planar interconnecting portion 81 that is on an angle so as to connect the portions 84 and 86 together.

As depicted in FIGS. 12a and 12b, base plate 90 includes first portion 86 configured as a substantially horizontal plane that is below the second substantially horizontal plane of the second portion 84 such that media, cells and the like 105 will evenly disperse along the upper surface of base plate 90 because angled portion 81 prevents cells and media 105 from pooling on portion 84. When the flask 110 is in use as depicted in FIGS. 12a, 12b and 15, first portion 86 of base plate 90 is the lowermost portion of the interior 120 of the device 110.

As depicted in FIGS. 16a and 16b, when flask 110 is placed on one side as shown in FIG. 16a each tray equally fills with media 105. Alternatively, when flask 110 is placed in an upright position as shown in FIG. 16b, each tray equally fills with media 105 again.

As shown in FIGS. 10, 12a and 12b, a portion of the interior 120 contains one or more cell growing trays 92. These trays have a substantially flat bottom portion 76, a substantially planar lip portion 78 that is on an upward angle away from the substantially flat bottom 76 of each tray 92, and sidewalls 97 that run around the periphery of the tray 92. The lip portion 78 has an interior edge portion 99. The number of sidewalls 97 of the tray(s) 92 is equal in number to the number of sidewalls of the flask 110. The front sidewall 87 of the tray(s) is different than the rest of the sidewalls 97 of the tray(s) 92 in that it is angled outward and away from the interior swooping curvilinear edge 99 of the lip 78 of the bottom portion of the trays. The front sidewall 87 and the interior curvilinear edge 99 of the lip portion 78 provides open access or a gap region 89 to each tray for cells, liquids and gases 105 when arranged within the flask 110.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A cell cultivating flask comprising:
   a) a cover having a substantially horizontal surface and a resealable port;
   b) two or more identical intermediate trays each comprising a substantially flat portion, an upwardly angled lip, and a gap region, wherein the gap region is formed between the edge of the lip and a sidewall of the flask, and wherein at least a portion of the gap region aligns with the port; and
   c) a base tray comprising a first and second substantially flat portions, the second substantially flat portion located higher than the first substantially flat portion, and an interconnecting portion which is at an angle to interconnect the first and second portions, where at least a portion of the second substantially flat portion aligns with the port and the gap region.

2. The flask of claim 1, wherein the angle of the interconnecting portion in the base tray is from about 10 degrees to about 60 degrees.

3. The flask of claim 2, wherein the angle is from about 10 degrees to about 45 degrees.

4. The flask of claim 2, wherein the angle is from about 15 degrees to about 30 degrees.

5. The flask of claim 2, wherein the angle is about 22 degrees.

6. The flask of claim 1, wherein the resealable port further comprises a threaded cap.

7. The flask of claim 6, wherein the threaded cap comprises a gas permeable hydrophobic membrane or filter.

8. The flask of claim 7, wherein the gas permeable hydrophobic membrane or filter has a pore size less than about 0.65 microns.

9. The flask of claim 7, wherein the gas permeable hydrophobic membrane or filter has a pore size less than about 0.22 microns.

10. The flask of claim 1, wherein the flask comprises two intermediate trays.

11. The flask of claim 1, wherein the flask comprises at least four intermediate trays.

12. The flask of claim 1, wherein the flask comprises at least eight intermediate trays.

13. The flask of claim 1, further comprising a camera mounted to the cover or base tray.

14. The flask of claim 1, further comprising an overmolded plastic seal around the perimeter of the flask.

15. The flask of claim 1, further comprising a non-skid button on the base.

16. The flask of claim 1, further comprising non-slip gripping ribs.

17. The flask of claim 1, further comprising a lens in the cover or base tray.

* * * * *